US009808776B2

(12) United States Patent
Peters (10) Patent No.: US 9,808,776 B2
(45) Date of Patent: Nov. 7, 2017

(54) MIXING DEVICE FOR A CONTAINER, CONTAINER AND METHOD FOR INSTALLING THE MIXING DEVICE IN A CONTAINER

(71) Applicant: Jean-Marc Peters, Eupen (BE)

(72) Inventor: Jean-Marc Peters, Eupen (BE)

(*) Notice: Subject to any disclaimer, the term of this patent is extended or adjusted under 35 U.S.C. 154(b) by 470 days.

(21) Appl. No.: 14/497,406

(22) Filed: Sep. 26, 2014

(65) Prior Publication Data

US 2015/0093811 A1   Apr. 2, 2015

(30) Foreign Application Priority Data

Oct. 1, 2013  (DE) .................. 10 2013 219 938

(51) Int. Cl.

| B01F 7/00 | (2006.01) |
|---|---|
| C12M 1/107 | (2006.01) |
| C12M 1/00 | (2006.01) |
| C12M 3/00 | (2006.01) |
| C12M 1/06 | (2006.01) |

(52) U.S. Cl.
CPC ......... *B01F 7/00725* (2013.01); *C12M 21/04* (2013.01); *C12M 23/02* (2013.01); *C12M 23/34* (2013.01); *C12M 23/48* (2013.01); *C12M 27/06* (2013.01); *Y10T 29/49826* (2015.01)

(58) Field of Classification Search
CPC .................................................. B01F 7/00725
USPC .................................................. 366/285, 331
See application file for complete search history.

(56) References Cited

U.S. PATENT DOCUMENTS

| 859,943 | A | * | 7/1907 | Holden | .................. B01F 13/002 |
|---|---|---|---|---|---|
| | | | | | 366/281 |
| 2,154,535 | A | * | 4/1939 | Schutz | .................... C03B 5/187 |
| | | | | | 366/147 |
| 2,559,196 | A | * | 7/1951 | Medved | ................ A47J 37/101 |
| | | | | | 220/367.1 |
| 2,625,720 | A | * | 1/1953 | Ross | ........................ B41B 5/06 |
| | | | | | 222/318 |

FOREIGN PATENT DOCUMENTS

| DE | 8312809 u1 | 10/1983 |
|---|---|---|
| DE | 202004004101 U1 | 9/2004 |
| DE | 102004027077 A1 | 1/2006 |
| DE | 202006011144 U1 | 1/2008 |

(Continued)

*Primary Examiner* — David Sorkin
(74) *Attorney, Agent, or Firm* — Von Rohrscheidt Patents (57) ABSTRACT

A mixing device for an application in a container including a rotatable shaft; a drive device through which the rotatable shaft is drivable; and at least one mixing element arranged at the shaft, wherein the mixing element is rotatable together with the shaft, wherein the shaft includes a support device connected with the shaft, wherein the support device is arranged in an end portion of the shaft that is oriented away from the drive device, wherein the shaft is rotatable about its longitudinal axis relative to the support device, wherein the mixing device is supportable through the support device in a receiving device connected with the container, wherein the support device is moveable by a straight bearing or a rolling element bearing along a guide device into the receiving device, wherein the straight bearing includes at least one sliding surface that is moveable on a corresponding sliding surface.

3 Claims, 7 Drawing Sheets

(56) References Cited

FOREIGN PATENT DOCUMENTS

| DE | 102007034463 A1 | 1/2009 |
|----|----|----|
| DE | 202009010167 U1 | 11/2009 |
| EP | 2064308 A1 | 6/2009 |
| EP | 2636444 A1 | 9/2013 |
| WO | WO 2007110775 A2 | 10/2007 |
| WO | WO 2011139209 A1 | 11/2011 |

\* cited by examiner

MIXING DEVICE FOR A CONTAINER, CONTAINER AND METHOD FOR INSTALLING THE MIXING DEVICE IN A CONTAINER

RELATED APPLICATIONS

This application claims priority from and incorporates by reference German patent application 10 2013 219 938.4 filed on Oct. 1, 2013.

FIELD OF THE INVENTION

The present invention relates to a mixing device for an application in a container.

BACKGROUND OF THE INVENTION

Mixing devices and containers, in particular fermenters as described supra have been known in the art for quite a while and are used in particular in the field of biogas systems that are used for generating renewable energy.

Mixing devices as recited supra are subject to a certain amount of normal wear during operations. The wear occurs primarily in the bearings and in the transmission of the mixing devices. Depending on the quality of the mixing device, a failure occurs sooner or later due to a failure of at least one of the wear parts, unless a preventive replacement of wear parts is already performed prior to that. In case of a failure the wear parts have to be replaced in order to be able to operate the mixing device again. In fermenters with plural mixing devices, a temporary failure of an individual mixing device may be tolerable for a certain time period. The reduced circulation of the substrate arranged in the container, however, retards the desirable biological breakdown process which eventually leads to a reduction of the through-put and energy output of the biogas plant. Such losses significantly degrade the economics of the biogas system. A longer failure of a mixing device or even of plural mixing devices is therefore not acceptable.

Therefore, the failed mixing devices are repaired or replaced. For this purpose it is frequently required to open the fermenter, empty it and stop operations of the biogas plant. Shut-down times caused thereby induce significant cost which should rather be avoided.

A solution of this problem is taught for example by EP 2 064 308 A1 which describes a mixing device which can be changed during ongoing operations of the fermenter. This is achieved in that a lower end of the shaft of the mixing device which is oriented towards a base plate of the container and which end together with a rotation bearing is configured as a bearing cartridge inserted into the hollow shaft forms the bearing device wherein the lower end of the shaft is loosely inserted into a receiving device of the container. This receiving device is configured to block a rotation of the support device of the mixing device wherein the support device is configured as a rolling element bearing in order to support the mixing device. However, the mixing device can be easily lifted out of the receiving device without having to take particular measures. In particular, it is not required to disengage the mixing device at its lower end from the receiving device through tools or similar.

The known configuration, however, has disadvantages in that it requires on the one hand a mandatory vertical operating position of the mixing device shaft and on the other hand requires a fermenter whose ceiling device is formed by a rigid concrete ceiling. This rigid concrete ceiling is used as a framework for receiving the mixing devices which are lowered from the top side into the fermenter. A ceiling configuration of this type is disadvantageous in that it requires on the one hand side a high level of planning and has to be computed and planned for each container of each project separately, and on the other hand delays the construction of the fermenter since a ceiling structure of this type is rather difficult to produce.

From this point of view, fermenters of this type with membrane closures are very advantageous. Membranes of this type are connected gas-tight to circumferential walls of the fermenter and then bulge outward due to biogas forming in the interior cavity of the fermenter and form so-to-speak a tent roof over the fermenter. Constructing a ceiling device of this type in the form of a flexible membrane can, therefore, be performed in a much quicker and cost-effective manner. Furthermore, most of the planning complexity recited supra can be omitted. However, using vertically oriented mixing devices is not possible in plants of this type since supporting the mixing device at its upper end cannot be performed easily without a frame structure. Namely, the membrane itself is not configured to react incurred support forces.

Therefore, fermenters that are enclosed with membranes of this type are typically operated with mixing devices which are configured for circulating the substrate wherein the mixing devices are laterally inserted into the fermenter through the wall. For this purpose slanted mixing devices and also so-called rod mixing devices can be used. Slanted mixing devices are known for example from the documents DE 20 2004 004 101 U1 and WO 2007/110775 A2. These illustrate mixing devices which are laterally run through the walls of the respective fermenter out of the inner cavity in outward direction and which are supported in or at the walls. The illustrated systems, however, have the disadvantage that the fermenter can only be filled up to a relatively low filling level which terminates in any case below the lateral mounting opening in the wall of the container. The height of the fermenter can, therefore, only be used partially. Furthermore, there is a problem in that due to the configuration inherent closeness of the shaft of the mixing device to the wall of the container in the upper end section of the mixing device, the associated mixing elements are arranged very close to the walls. The associated mixing elements, however, have to be arranged at least far enough from the wall so that they do not impact the wall when the shaft of the mixing device rotates.

Furthermore, a heatable mixing device for fermentation containers is known from DE 10 2004 027 077 A1, wherein the mixing device is provided for introducing mechanical and also thermal-energy into a fermentation container. The known mixing device includes a heatable mixing shaft and heat-conducting surfaces attached to the mixing shaft wherein mixing blades are arranged at the mixing shaft. In installed position, the shaft axis is inclined relative to vertical by an angle of approximately 45°. The shaft support is arranged in a bearing base (so-called mounting block) fixated at the container. The inclination angle of the lower support device fixated at the container is adjustable during assembly when the fermentation container is empty. After the bearing is worn out, the container has to be emptied in order to be able to replace the bearing device.

The same problem of mandatory container or reactor emptying occurs in the mixing device according to DE 10 2007 034 463 A1. A lower element of the bearing device is fixated at the container base so that a replacement is not possible when the reactor is full. Furthermore, the mixing device is vertically oriented in installed position.

DE 82 12 809 U1 discloses a mixing device in which a base mounted support device is provided. It is an object of the invention described in this document to facilitate a flow direction in the substrate to be mixed which flow direction is parallel to the mixing device shaft. When the base mounted bearing device is damaged, the container has to be emptied in order to perform a replacement of the bearing device.

DE 20 2006 011 144 U1 teaches a mixing device in a slanted installed position with a bearing device that is fixated at the container. This causes the problems recited supra when a bearing is damaged or when a routine bearing change needs to be performed.

DE 20 2009 010 167 U1 teaches a mixing in a so-called submerged motor configuration wherein a mixing device mast is rotatably supported on a pinion at a base and configured to be rotated by a first crank. The mixing device which is moveably supported in longitudinal direction of the mast at a sleeve can be optionally removed out of the fermentation mass through a pull cable or lowered into the fermentation mass. A slanting of the mixing device in its operating position is neither provided nor helpful. Also EP 2 636 444 A1 discloses a submerged motor mixing device of this type.

Last not least WO 2011/139209 A1 discloses a suspended mixing device whose lower end is suspended at the container base with a spring-loaded chain. On the one hand it is necessary to empty the container when a bearing at the bottom side of the mixing device shaft is worn, and on the other hand the suspended support for receiving the tension forces impacting the mixing device requires a high load-bearing configuration for the upper mixing device attachment which can typically only be configured as a concrete ceiling for the fermentation tank. A slanted arrangement of the mixing device is not provided.

BRIEF SUMMARY OF THE INVENTION

Thus, it is an object of the invention to provide a mixing device and a container, in particular a fermenter which facilitates exchanging the mixing device in a simple manner during operations and which facilitates using a very simple configuration for the ceiling device of the container.

The object is achieved with a mixing device according to the invention wherein an angle between the longitudinal axis of the shaft and vertical is increased during transferring the mixing device from a mounting position into an installed position, and wherein the angle in the installed position is advantageously between 5° and 60°, further advantageously between 10° and 50°.

The object is achieved by a mixing device for an application in a container, the mixing device including a rotatable shaft; a drive device through which the rotatable shaft is drivable; and at least one mixing element arranged at the shaft, wherein the mixing element is rotatable together with the shaft, wherein the shaft includes a support device connected with the shaft, wherein the support device is arranged in an end portion of the shaft that is oriented away from the drive device, wherein the shaft is rotatable about its longitudinal axis relative to the support device, wherein the mixing device is supportable through the support device in a receiving device connected with the container, wherein the support device is moveable by a straight bearing or a rolling element bearing along a guide device into the receiving device, wherein the straight bearing includes at least one sliding surface that is moveable on a corresponding sliding surface of the guide device or the rolling element bearing includes at least one running roller that is rollable on a rolling surface of the guide device.

Furthermore, the object is achieved by a container, in particular a fermenter for fermenting biodegradable substances, the container comprising at least one base plate, at least one wall and at least one ceiling device, wherein an interior cavity of the container is essentially enclosed gas-tight by the base plate, the wall, and the ceiling device, wherein the container includes at least one mixing device which is configured to mix substances arranged in the inner cavity of the container, wherein the ceiling device is formed by at least two ceiling units, namely at least one plate unit and at least one membrane unit, wherein the plate unit is formed by a plate shaped element and the membrane unit is formed by a flexible membrane, wherein the plate unit and the membrane unit are connected with one another essentially gas-tight in portions where they contact each other.

Optionally the container can include a receiving device connected with the base plate through which receiving device a support device of the mixing device is receivable, wherein the support device is arranged at an end portion of the shaft of the mixing device, which end portion is oriented towards the base plate of the container; and optionally a guide device through which the support device of the mixing device is movable towards the receiving device during a transfer of the mixing device from a mounting position into an installed position, wherein the receiving device is arranged at one end of the guide device and defines the installed position of the mixing device in which the receiving device blocks an unintentional movement of the support device.

Last not least the object is achieved by a method for installing a mixing device in a container, in particular a fermenter including the following method steps:

a) supporting a support device of the mixing device in a receiving device of the mixing device which receiving device is connected with the base plate of the container, which support device is arranged at an end of a shaft of the mixing device which end is oriented towards the base plate of the container and connected with the shaft, initially inserting the support device into a guide device of the mixing device starting from a mounting position of the mixing device in order to insert the support device of the mixing device into the receiving device and guiding the support device through the guide device in a direction towards the receiving device which is arranged at an end of the guide device until the support device reaches the receiving device and is received by the receiving device so that the mixing device is in its installed position.

b) supporting the mixing device in its upper support section that is oriented away from the base plate.

The invention is subsequently described with reference to an embodiment of a fermenter, in particular for bio gas plants without the invention being limited to an application in fermenters. The mixing device according to the invention is also suitable for a plethora of other mixing applications.

As stated supra, the invention was motivated by the desire to simplify a support of the mixing devices of a container. In any case, the support includes an upper end of the container which needs to be attached to react operational forces of the mixing device. This reaction is the more complicated, the further the upper end of a respective container that needs to be supported is offset from the wall of the associated fermenter. This comes from the fact that the forces that need to be reacted have to be reacted over larger distances into the wall of the respective container. Consequently, there is a desire to arrange the upper end of the mixing device as close to the wall as possible, optionally even in the wall, this means to introduce support forces directly into the wall. Therefore, it is conceivable as a matter of principle to run the upper end of the mixing device at a "top side" or "laterally" out of the respectively associated fermenter. Both variants can be advantageous depending on the type and size of the container. However, supporting the mixing device as close to the wall of the container as possible has two disadvantages. On the one hand, as stated in the discussion of the prior art there is the risk that mixing elements of the mixing device hit the wall of the container. Consequently, a certain minimum distance between two components has to be provided at all times. On the other hand, the mixing effect of the mixing device is limited to an edge portion of the container when the mixing device is arranged close to the wall, whereas substrate arranged in a center portion of the container remains substantially unmixed.

There is a desire for the mixing device according to the invention to position it in a certain minimum distance from the wall of the fermenter when the mixing device is in its installed or operating position in which it is completely mounted in the fermenter so that the at least one mixing element of the mixing device has sufficient distance from the respective most proximal wall of the fermenter and is not prone to hit the wall of the fermenter. Furthermore, it is desirable as a matter principle not to limit the mixing action of the mixing device to edge portions of the fermenter, but to achieve the mixing effect also in a center portion of the fermenter. Simultaneously it is also desirable to arrange the upper end of the mixing device not too far from the wall of the fermenter since in this case of a rigid ceiling device which is configured for reacting support forces of the upper end of the mixing device into the wall of the fermenter would have to be run by the same distance away from the wall of the fermenter in order to receive the upper end of the mixing device. A flexible ceiling device, for example configured as a flexible membrane is not suitable for receiving bearing forces of a mixing device. However, only receiving the support forces of the mixing device with a rigid ceiling device does not suffice. These support forces then have to be reacted in any case from the ceiling device into the wall of the fermenter. This is the more difficult the further the upper end of the mixing device is arranged away from the wall and the further the bearing forces have to be conducted by the rigid ceiling device. Thus, there is the issue to arrange the mixing device as far from the wall of the fermenter as possible in order to achieve a mixing effect in the center portion of the fermenter, but to remove it not too far from the wall to facilitate its support.

The solution according to the invention is based on the idea to insert the mixing device into the container, in particular the fermenter, during its assembly as close as possible to the wall suspended from a lifting device and oriented in a direction that is as vertical as possible. The mounting position is reached as soon as the upper end of the mixing device shaft contacts the guide device with the straight bearing or rolling element bearing arranged at this location during lowering the mixing device. Thereafter, only the lower end of the mixing device is moved away from the wall while the upper end of the mixing device stays at least proximal to the wall. Therefore, the solution according to the invention includes a mixing device that is oriented at a slant angle in its final operating position whose longitudinal axis of the shaft is arranged at an angle relative to vertical. Energy that is required for moving the lower end of the mixing device shaft can be generated by a conversion from potential energy when the guide device is provided at an excessively steep angle in a direction towards the receiving device. According to this solution, a mixing effect achieved through the at least one mixing element is also provided outside of the edge portion of the fermenter since the mixing device due to its slanted position extends at least partially in a direction of the center portion of the container and can cause a mixing of the substrate at this location. Simultaneously a ceiling device that is provided for receiving an upper end of the mixing device can be configured rigid only in an edge portion of the container, wherein a rigid ceiling unit of this type does not have to extend significantly from the wall in a direction of the center portion of the fermenter. A remaining portion of the ceiling device can thus be formed by the flexible ceiling unit, in particular a flexible membrane. Optionally, even a support of the upper end of the mixing device can be provided directly in the wall of the container so that the rigid ceiling unit can be omitted almost completely, wherein only a section has to remain which is used for mounting or dismounting the mixing device. This is conceivable in particular for tall fermenters, typically taller than 8 meters that are not filled with substrate over their entire height and for which a lateral attachment of the upper end of the mixing device therefore has no disadvantages. In this case, the ceiling device of the fermenter can be accordingly formed by a flexible membrane almost in its entirety.

The movement of the mixing device that is oriented away from the wall of the fermenter during the mounting process is provided according to the invention with the straight bearing or rolling element bearing of the support device. The sliding device includes a sliding surface which is suited particularly well to slide on a corresponding sliding surface with low sliding friction. In particular, the sliding surface should be as smooth as possible. Alternatively the recited rolling element support is feasible which includes at least one rolling element which is configured to roll on a corresponding rolling surface. The rolling surface can be formed for example by the base plate of the container. By the same token it is hardly conceivable to move the mixing device with its high mass in a controlled manner over an essentially flat surface of the base plate of the container, in particular because installing the mixing device shall also be possible when the container is filled so that substrate included in the container causes a substantial resistance against an intended movement of the lower end of the mixing device. Therefore, the container advantageously includes a guide device through which the sliding surface of the sliding support or the running roller of the rolling element support and thus, the bearing device and eventually the entire mixing device can be guided in a particularly simple manner. A variant of this type is subsequently described in detail.

Eventually it is intended to move the support device of the mixing device through the straight bearing or rolling element bearing into an installed position in which the support device subsequently remains so that the mixing device can be put in service. This method is comparable to the method of EP 2064 308 B1. Thus, it is particularly advantageous when the support device is insertable or pushable into a receiving device through the straight bearing support or rolling element bearing support, wherein the support device can then be supported in the receiving device without tools so that support forces are reactable and in particular a torque-proof connection is required. This means that the shaft of the mixing device is drivable and thus rotatable by a drive device in the installed position of the support device, wherein the support device itself is mounted torque-proof, thus not co-rotating with the shaft of the mixing device but fixated. Thus, the support device itself is configured as rolling element bearing that is attached to the shaft (bearing cartridge). Due to the inclined arrangement it can be required to react upward oriented lifting forces which can be caused due to a mixing of the substrate. This is typically performed with the bearing of the upper end of the mixing device but can also be additionally achieved with a blocking device which is arranged at the receiving device of the lower end of the mixing device. Disassembling the support device from the receiving device without tools and subsequent back sliding of the sliding surface or backward rolling of the running roller on the support device is therefore easily feasible so that replacing the mixing device without impairing operations of the biogas system can be easily provided.

Therefore, the mixing device according to the invention provided with the sliding bearing or the roller bearing has the following advantages:

The ceiling device of the container, in particular the fermenter can be largely, optionally even completely formed by a flexible membrane. A rigid ceiling portion is required for supporting the upper end of the mixing device according to the invention at the most in an edge portion of the container.

The mixing device is attachable with its lower support device without tools in the container and fixable in its operating position. Replacing the mixing device or individual components thereof, therefore does not require a use of tools and thus no emptying and cleaning of the container.

In spite of the upper end of the mixing device being proximal to the closest wall of the container, optionally even the support of the upper end in the wall, the at least one mixing element of the mixing device also develops a mixing effect at a certain distance from the wall of the container. Therefore, the mixing effect is not locally limited to an edge portion of the container.

In a mixing device according to the invention in which at least one mixing element is formed by a plate-shaped paddle element which is connected torque-proof with the shaft through a retaining device, a linking device is particularly advantageous through which an angle that is enclosed by the shaft and at least one partial section of the retaining device is variable. This variability of the orientation of the mixing element relative to the shaft of the mixing device facilitates a compensation for a slanted arrangement of the mixing device in case this is necessary and/or desired. In particular it is possible to angle the mixing element far enough so that it does not exit from a surface of the substrate when the shaft turns. By the same token, angulation can be advantageous in order to reduce a horizontally measured distance between a connecting location of the support device at the shaft and an edge portion of the mixing element that is removed the farthest from the shaft so that the edge portion of the mixing element is not at risk of impacting the wall of the container.

With respect to the rolling element support it is particularly advantageous when a running surface has at least one running roller through which it is rollable on a corresponding rolling surface is configured concave or convex. A running roller thus configured is suited particularly well to interact with an accordingly configured rolling surface forming partial form-locking. For example, it is conceivable that the rolling surface is shaped convex, wherein the convex section advantageously has the same curvature radius as the associated concave-shaped running roller which consequently conforms with its surface to the rolling surface and is laterally stabilized due to the complimentary shaping of the corresponding components. A controlled support of the running roller is thus implemented in a particular simple manner.

It is also conceivable that the rolling element support has plural running rollers which respectively roll on a rolling surface. This rolling can also occur in lateral direction, this means a contact surface between the running roller and the rolling surface can be oriented vertically. Any other orientation, in particular a slanted orientation of the contact surface at an angle of 45° is also conceivable.

Improving upon on a container, in particular fermenter of the type described supra, the object is achieved according to the invention in that the mixing device is arranged inclined relative to vertical, wherein the vertical and a longitudinal axis of a shaft of the mixing device enclose an angle between 5° and 60°, wherein at least a portion of the at least one plate unit which includes the mounting opening is oriented perpendicular to the longitudinal axis of the shaft. A subdivision of the ceiling unit and the membrane unit is provided according to the invention for a mixing device whose upper end is supported at a top side of the container. When the mixing device is supported in the wall of the container the subdivision according to the invention is typically provided, the plate unit, however, is not configured for receiving support forces. Instead, the plate unit is essentially only required for mounting or dismounting the mixing device. This means also in case the mixing device is supported in the wall of the container the ceiling device is typically formed by two separate ceiling units, wherein the plate unit only has to function to provide an inlet opening for the mixing device, wherein the mixing device can be lowered through the inlet unit during installation into the container. An attachment of the upper end of the mixing device is then performed in the wall of the container, for example in a frame that is installed in the wall into which the upper end of the mixing device is insertable from above and attachable thereon.

The ceiling device according to the invention facilitates using the advantages of the membrane unit in as far as this is permitted by the operating position of the mixing devices. The plate unit is only required in order to reliably support the upper end of the mixing device or of the mixing devices, this means to react the effective bearing forces. A support of this type, this means receiving bearing forces cannot be provided by the membrane unit. As recited supra, the subdivision is particularly useful when the plate unit is arranged as close as possible to the wall of the container. This significantly reduces load-reaction through the plate unit into the walls.

Thus, it is particularly advantageous when the plate unit is arranged parallel to the base plate. A plate unit of this type is producible in a fairly simple manner.

In an advantageous embodiment of a container, in particular fermenter according to the invention its plate unit includes at least one mounting unit through which the mixing device is insertable from an outside of the plate unit from above into the inner cavity of the container. An opening of this type is particularly well suited to be able to mount the mixing device. Alternatively, a lateral docking of the mixing device at the plate unit is conceivable. However, load-introduction and also connecting the membrane unit to the plate unit is simpler when the mixing device is fixated in a mounting unit which is surrounded by the plate unit.

Thus, it is particularly advantageous for the mounting opening when the mounting opening is configured rectangular, wherein a free cross-section of the mounting opening which remains after inserting the mixing device into the container, and which connects the inner cavity of the container with the outside of the plate unit is essentially closeable gas-tight. The rectangular cross-sectional shape of the mounting opening is advantageous in as far as its surface can be kept as small as possible while maintaining sufficient space for the mixing device to be inserted. As a matter of principle, a mixing device only has one mixing element at a location along its shaft, this means two mixing elements are not arranged at the same level of the shaft, this means not directly adjacent to one another. In top view of the mixing device, the individual mixing elements, in case several of them are provided, are typically arranged offset from the adjacent mixing elements by an angle of 180° about the shaft of the mixing device. Alternatively, an offset of 90° or by any other angle is conceivable, though this is rather untypical. Advantageously the mounting opening is sized large enough so that the shaft including a mixing element connected therewith just barely fits through the mounting opening. Thus, it is necessary that the mixing device is continuously moved in lateral direction during insertion into the container in order to respectively position the next mixing element (in case provided) relative to the mounting opening so that it fits through the mounting opening and does not collide with the plate unit. In a mixing device in which the mixing elements are offset by 90°, a purely lateral movement of the mixing device during insertion into the fermenter does not suffice, instead a rotation of the mixing device has to be additionally provided about the longitudinal axis of the shaft in order to align the respective next mixing device element relative to the mounting opening. Alternatively it is also conceivable that the mounting opening has dimensions that facilitate inserting the mixing device without the mixing device having to be moved into particular positions. However, a mounting opening of this type would have to be sized significantly larger and would consequently weaken the plate unit. Furthermore, sealing the mounting opening is the more difficult the larger the mounting opening is selected.

According to the descriptions already provided supra, it is particularly advantageous when the mixing device is arranged inclined relative to vertical, wherein the vertical and a longitudinal axis of a shaft of the mixing device enclose an angle between 5° and 30°, wherein at least a portion of the at least one plate unit which includes the mounting opening is oriented perpendicular to the longitudinal axis of the shaft. The slanted arrangement facilitates to move a lower end of the mixing device as far as possible in a direction towards a center portion of the fermenter, place it there and simultaneously leave an upper end as close as possible to the wall of the fermenter.

As already apparent from the preceding description, a container according to the invention is particularly advantageous when an upper end section of the container which is oriented away from the base plate of the container is connected with the plate unit in a force-transmitting manner. The plate unit functions as a support for the upper end of the mixing device and can receive respective support forces. Additionally, the mixing device is supported with its support device at its lower end. Alternatively it is also conceivable that the upper end of the mixing device is directly connected with the wall of the container in a force-transferring manner, thus supported in the wall. Thus, the upper end in an operating position of the mixing device in which it is completely mounted is laterally run out of the fermenter, namely out of a portion of the wall of the container. Since as recited supra, the lower end of the mixing device is moved through its support device in a direction of a center portion of the container, this yields a slanted position of the mixing device which is enlarged compared to a top side support of the mixing device, this means a support of the upper end in the ceiling device.

Improving upon a container, in particular fermenter of the type described supra the objective can also be achieved by a guide device through which the support device of the mixing device can be guided during the installation of the mixing device into the container in a direction towards the receiving device, wherein the receiving device is arranged at an end of the guide device and fixates an installed position of the support device in which it blocks an unintentional movement of the support device. A guide device of this type is already described supra. It is particularly well suited to guide the rolling element support of the mixing device into the receiving device where the support device of the mixing device can take its installed position. According to the invention, an angle between vertical and a longitudinal axis of the shaft of the mixing device increases while transitioning the mixing device from the mounting position into the installed position so that the mixing device in its operating position in which it is completely mounted and ready for operation, is arranged inclined relative to vertical and the vertical and the longitudinal axis of the shaft of the mixing device enclose an angle between 5° and 60°, advantageously between 10° and 50°. The inclination is a consequence of the advantageous support of the mixing device already described supra, whose lower end is arranged as far as possible from the closest wall of the container, whereas its upper end is arranged as close as possible to the closest wall of the container, possibly even in the wall. An inclination of the mixing device in the container according to the invention in the range described supra yields the desired result for the height dimensions of typical containers.

As a matter of principle installing a guide device is independent from the configuration of the ceiling device, in particular the question whether the ceiling device is formed by at least two ceiling units (plate unit, membrane unit). In a particularly advantageous configuration of the container according to the invention, the container includes both, this means a divided ceiling device as described supra and also a guide device as described supra.

The container according to the invention is particularly advantageous when the guide device includes an elongated sliding unit or an elongated rolling unit, advantageously a running tube, wherein the sliding unit is advantageously smooth and the rolling tube advantageously has a convex or concave rolling surface. The advantage of this embodiment of the guide device has already been described supra.

The guide device is particularly advantageous when it has an inclination angle relative to horizontal at least in a portion of a guide section of at least 5°, advantageously at least 7.5°, further advantageously at least 10°. Thus, the guide section is the section of the guide device which includes a sliding surface for the at least one corresponding sliding surface of the sliding bearing or a rolling surface for the at least one running roller of the rolling element bearing of the mixing device. An inclination of at least a portion of the guide section or advantageously of the entire guide section is particularly advantageous since the mixing device with its sliding or rolling element bearing is supportable in a guide device of this type in a particularly simple manner. The reason is that the force of the weight impacting the mixing device in a slanted guide device includes a vector portion in a direction of the guide device wherein the vector portion eventually supports the mixing device on the guide device by itself. After placing the sliding or rolling bearing on the guide device, the sliding or rolling bearing will move along the guide device by itself. An additional force application by the technician assembling the mixing device is not required, but only required to a small extent.

In a particularly advantageous embodiment of the container according to the invention the receiving device is arranged at a distance of at least 1.5 m perpendicular from the at least one wall, advantageously at least 2.0 m, further advantageously at least 2.5 m from the wall of the container. The receiving device is thus typically connected directly with the base plate of the container. Maintaining the described minimum distance means that the support device of the mixing device in its installed position is installed at least at the same distance from the wall of the container so that it is assured that a mixing effect of the mixing elements can not only be developed in an edge portion of the container, but also in a center portion of the container.

The object of the invention is achieved by a method for installing the mixing device including the following method steps:

c) While transferring the mixing device (1,1') from the mounting position into the installed position an angle between vertical and a longitudinal axis of the shaft (12) is increased, wherein the angle in the installed position of the mixing device (1, 1') is advantageously between 5° and 60°, further advantageously is between 10° and 50°.

This method step can already be derived from the preceding description and emphasizes that the mixing device can be inserted in a particularly simple manner into an edge portion of the container, wherein the mixing device is essentially oriented vertical in a mounting position, this means before and when the support device impacts the guide device and only assumes a slanted position by sliding down the sliding surface or the support roller rolling on the guide device which leads away from the wall of the container. The upper end of the mixing device essentially remains at the same position and is not moved away from the wall of the container in analogy to the lower end. This yields a pivoting of the mixing device against vertical about a pivot point that is arranged approximately at the upper end of the mixing device. The method further facilitates that a mounting opening for inserting the mixing device into the interior of the container only has to be provided in an edge portion of the container since a movement of the mixing device is only provided in the container, this means aided by the guide device.

Thus, it can be particularly advantageous to lower the mixing device into the container from its top side at a distance of 2 m at the most measured perpendicular to a wall surface of a wall of the container, wherein, after the support device has reached its installed position an end of the mixing device that is oriented away from the base plate of the container, this means an upper end of the mixing device, is moved orthogonal to the wall surface of the wall of the container in a direction towards the center portion of the container and fixated thereafter. Such movement of the upper end of the mixing device can be advantageous in some cases when there is otherwise a risk that the at least one mixing element hits the wall of the container. A movement of the upper end in a direction of the center portion of the container does not occur by the same amount as for the lower end of the mixing device. Consequently the shaft of the mixing device stays in a slanted position in any case also for such movement of the mixing device.

It is appreciated that uninstalling the mixing device can be performed exactly in reverse to its installation. This means that the sliding bearing for the rolling element bearing with its at least one sliding surface or running roller initially leaves the receiving device of the container when uninstalling the mixing device and moves thereafter along the guide device in a direction towards the closest wall of the container. By the same token it is conceivable that the mixing device is lifted at its upper end so that the support device initially disengages from the receiving device and is then moved "free floating" in the substrate wherein an approximately vertical orientation of the mixing device is achieved self-acting due to the weight of the mixing device. In comparison to installing the mixing device this method is conceivable since the support device does not have to be moved to a particular location in the same manner. Thus, it would be very difficult during installation of the mixing device to place the support device into the receiving device in a controlled manner without using the guide device.

BRIEF DESCRIPTION OF THE DRAWINGS

The mixing device according to the invention, the container according to the invention and the method according to the invention are subsequently described based on an embodiment of a mixing device to be installed in a fermenter with reference to drawing figures, wherein.

DETAILED DESCRIPTION OF THE INVENTION

The embodiment illustrated in FIGS. 1-5 includes a representation of an installation of a mixing device 1 according to the invention and also an illustration of its operating position.

Figure 1:
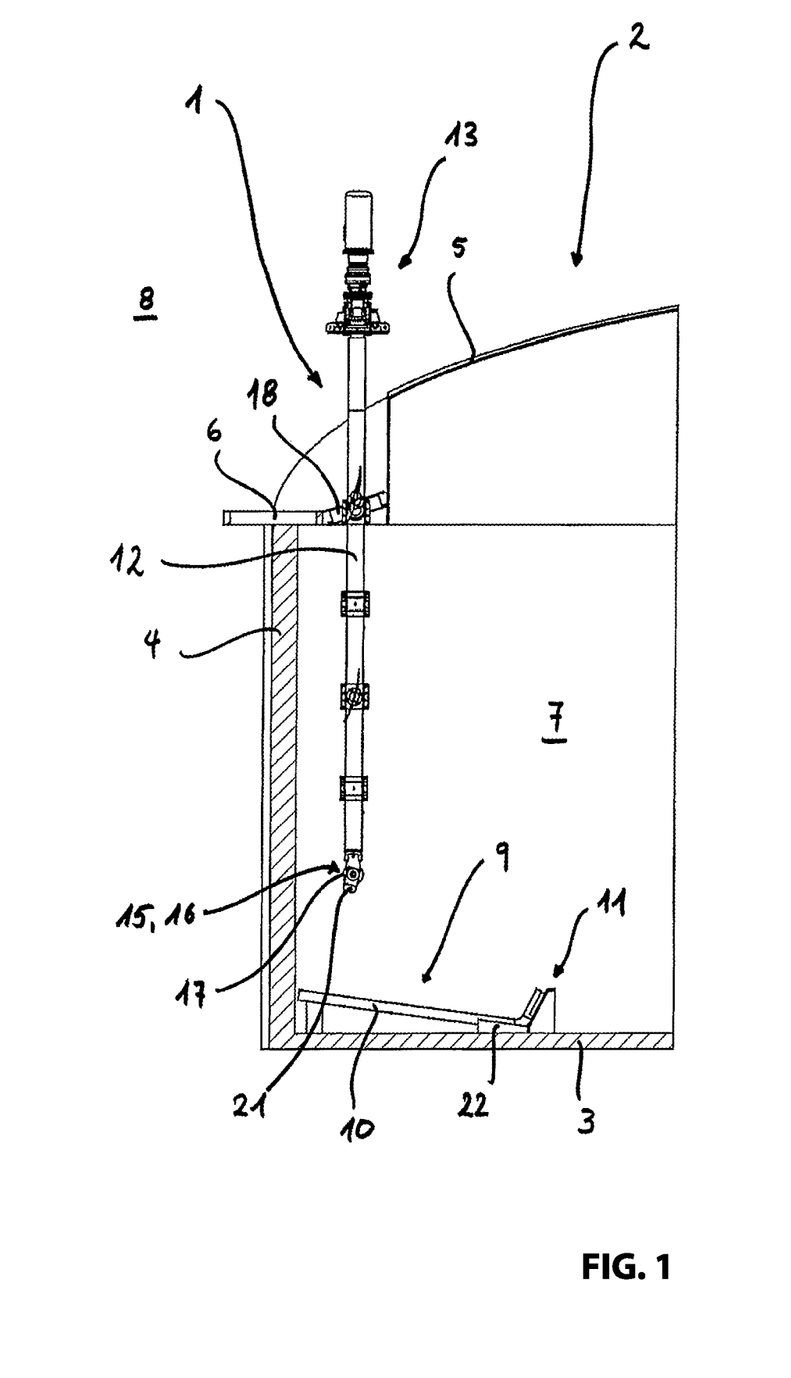
FIG. 1 illustrates a lateral view of a mixing device according to the invention that is arranged in a mounting position wherein the mixing device is being inserted into a container configured as a fermenter according to the invention.
Figure 2:
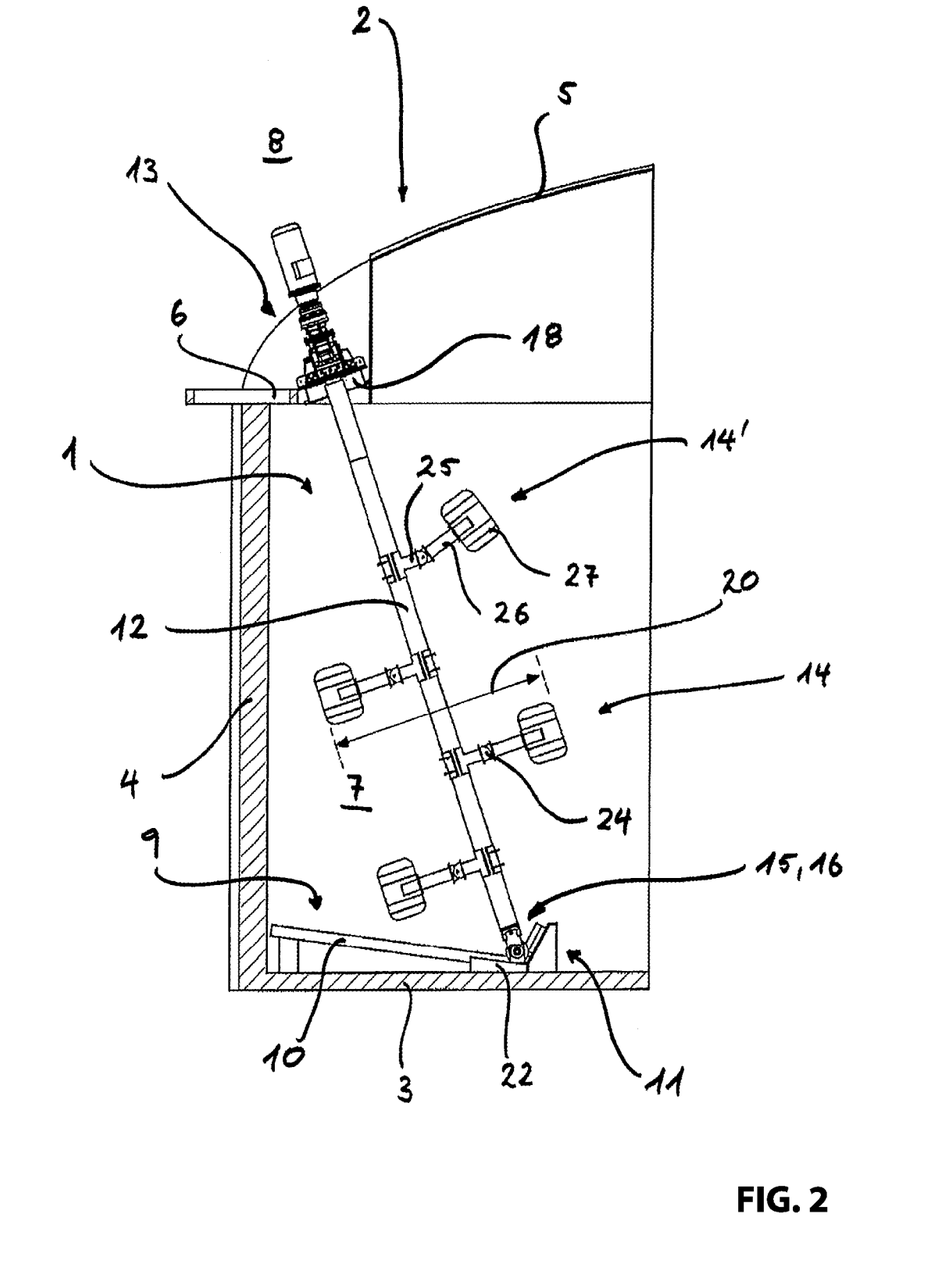
FIG. 2 illustrates a lateral view of the same mixing device, however in its operating position.

FIG. 1 illustrates the mixing device 1 according to the invention in its mounting position, wherein the mixing device 1 is first being installed into a fermenter 2 according to the invention. The fermenter 2 includes a baseplate, a circumferential wall 4 and a two component ceiling device. The ceiling device is formed by two ceiling units namely on the one hand side a membrane unit 5 and on the other hand side a plate unit 6. The ceiling device is essentially connected gas tight to the circumferential wall 4 of the fermenter 2. Essentially means that an inner cavity 7 of the fermenter 2 is sealed against an ambient 8 of the fermenter 2 so that an accumulation of gases formed in the fermenter 2 can occur in the interior 7. An uncontrolled exit of the formed gases formed from the interior cavity 7 into the ambient 8 is not possible. However, a certain amount of leakage may occur between the inner cavity 7 and the ambient 8 which however is small enough so that no significant volume flow can move from the inner cavity 7 into the ambient 8. The membrane unit 5 and the plate unit 6 are essentially connected gas tight with one another and form the tight ceiling device in this manner.

A guide device 9 which is connected with the base plate 3 is arranged in the fermenter 2 wherein the guide device is associated with the mixing device 1. The guide device 9 is formed by an elongated support tube 10 whose longitudinal axis in top view of the container 2 is oriented perpendicular to the wall 4. It is apparent from the view in FIG. 1 that the guide tube 10 is inclined at an angle relative to horizontal which angle is approximately 8°. An orientation of the guide tube 10 is thus provided so that a vertically measured distance between the base plate 3 of the container 2 and the guide tube 10 decreases with increasing distance from the wall 4 of the fermenter 2. At an end of the guide tube 10 of the guide device 9 that is oriented away from the wall 4 of the fermenter 2 a receiving device 11 is arranged that is also associated with the mixing device 1 wherein a functionality of the receiving device 11 in cooperation with the mixing device 1 is described infra in detail.

The mixing device 1 includes a shaft 12, a drive device 13, four mixing element 14 and a support device 15. The drive device 13 is arranged at an upper end of the shaft 12 of the mixing device 1 which is oriented away from the base plate 3 of the container 2. The shaft 12 is configured rotatable about a longitudinal axis of the shaft 12 relative to the drive device 13, wherein the shaft is rotatable or drive able through the drive device 13. The drive device 13 includes in particular an electric motor and a transmission whose details are known and therefore not relevant for the application.

At a lower end of the shaft 12 of the mixing device 1 that is arranged opposite to the drive device 13 a support device 15 is arranged. In the mixing device 1 according to the invention the support device 15 is formed by a rotating bearing which is inserted into the hollow shaft 12 as a bearing cartridge and thus removable from the fermenter 2 together with the shaft 12. A rolling element support 16 which includes a roller 17 is arranged at the support device 15. The support device 15 is configured rotatable in analogy to the drive device 13 about the longitudinal axis of the shaft 12 relative to the shaft 12. This way the support device 15 and the rolling element 16 can be used to support the lower end of the mixing device 1 torque proof in cooperation with the respective receiving device 11 so that a rotation of the shaft 12 is not blocked, this means that the support device 15 is supported with its outer portion in the receiving device 11 so that it stands still during the rotation of the shaft 12, wherein an inner portion of the support device 15 rotates together with the shaft 12 about its longitudinal axis.

It is apparent from FIG. 1 that the mixing device 1 during its installation into the container 2 is lowered through a mounting opening 18 of the plate unit 6 from the ambient into the inner cavity 7 of the fermenter 2. The mounting opening 18 has a rectangular cross section which is particularly apparent from FIGS. 3 and 4. A horizontally measured distance of the mounting opening 18 from the wall 4 of the container 2 is approximately 1.0 meters. The mounting opening 18 is arranged in an edge portion of the plate unit 6, which implicitly defines the function of the plate unit 6. The plate unit 6 namely mostly fulfills the purpose relative to the membrane unit 5 to provide a bearing for the mixing device, this means to be able to receive bearing forces. This is described in more detail infra.

Figure 3:
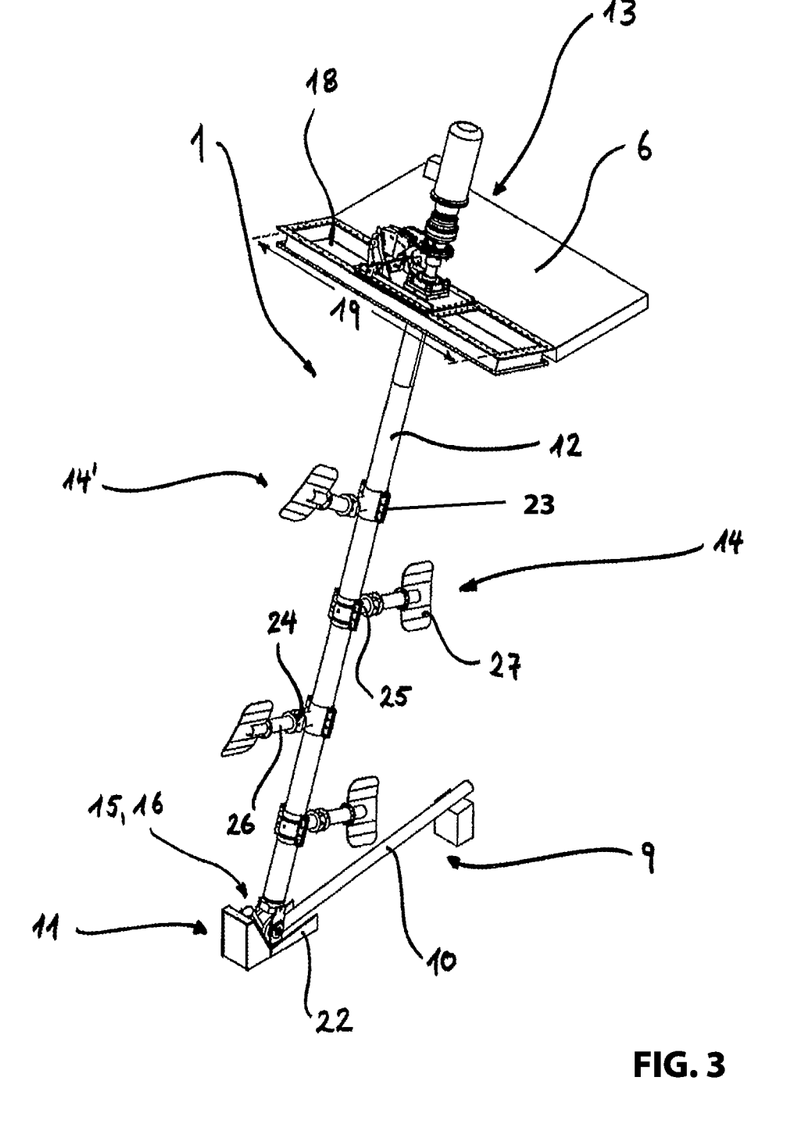
FIG. 3 is an illustration analogous to FIG. 2, however in a simplified isometric view.

The geometry of the mounting opening 18 is evident from FIG. 3. Here it is furthermore evident how the installation of the mixing device 1 into the fermenter 2 needs to be provided. A width 19 of the mounting opening 18 is selected only slightly larger than a distance 20 which is measured radially to the shaft 12 and which starting from an outermost location of a mixing element 14 which is most remote from the shaft 12 extends to an outermost location of an adjacent mixing element 14 which is also arranged most remote from the shaft 12. This distance 20 corresponds so to speak to a maximum width of the mixing device 1. Put differently the mounting opening 18 is sized so that the shaft 12 together with its mixing elements 14 fits through the mounting opening with its width so that there is no room to spare, wherein a movement of the mixing device 1 during its installation into the container 2 is not required in order to align the mixing elements 14 relative to the mounting opening 18. As an alternative it is also conceivable to configure the mounting opening narrower which has the consequence that the mixing device 1 during lowering into the inner cavity 7 of the container 2 continuously has to be moved laterally or in rotation in order to align one mixing element 14 after another, relative to the mounting opening so that a collision between the plate unit 6 and the mixing device 1 is avoided.

If mixing element, differently from the embodiment described supra are not arranged respectively offset by 180° relative to a respective adjacent mixing element about the respective shaft but are offset for example by 90° it is typically necessary to rotate the respective mixing device during installation or dismounting about the longitudinal axis of the respective shaft in order to align the mixing elements accordingly relative to the respective mounting opening.

The mixing device 1 is lowered essentially vertically through the mounting opening 18 into the fermenter 2 during installation. Shortly thereafter the rolling element support 16 contacts the guide device 9 or its guide tube 10. The running roller 17 and the guide tube 10 are adapted so that the roller 17 can roll easily on an outer enveloping surface of the guide tube 10. This enveloping surface forms so to speak the rolling surface for the running roller 17. As soon as a contact between the running roller 17 of the rolling element support 16 of the support device 15 of the mixing device 1 and the guide tube 10 of the guide device 9 is established it is particularly simple to move the support device 15 along the guide tube 10 or to roll it. The inclination of the guide tube 10 facilitates this movement since already the force of the weight of the mixing device 1 causes a rolling movement along the guide tube 10. A length of the guide tube 10 is approximately 3.0 meters in the illustrated embodiment.

The guide device 9 is thus particularly well suited to receive the support device 15 with the rolling element bearing 16 of the mixing device 1 and to guide it in a direction towards the receiving device 11 thereafter. As soon as the support device 15 has arrived in the receiving device 11 the support device 15 is in its installed position. This installed position of the support device 15 is visible particularly well in FIGS. 2-5. In the installed position of the support device 15 the support device 15 is positioned in the receiving device 11 so that a rotation of the support device 15 about the longitudinal axis 12 of the mixing device 1 is blocked. This effect is achieved in the illustrated embodiment through blocking plates 21 that are laterally arranged at the running roller 17 of the rolling element support 16, wherein the blocking plates extend from a rotation axis of the running roller 17 towards the base plate 3 of the container 2, wherein a length of the blocking plates 21 exceeds a radius of the running roller 17, so that a lower edge of the blocking plate 21 forms a lower spot of the mixing device 1. Put differently the mixing device 1 being lowered vertically onto a flat surface would reach the flat surface first with the lower edges of the blocking plates 21. As soon as the support device 15 is in its installed position the blocking plates 21 enter a form locking engagement with corresponding wall elements 22 of the receiving device 11. This form locking engagement eventually prevents a rotation of the support device 15 about the longitudinal axis of the shaft 12 of the mixing device 1 also when the running roller 17 with its wheel flanges would lift off from the support tube 10 and would lose its form locking engagement. This cooperation is evident in particular from the detail of FIG. 5.

Figure 5:
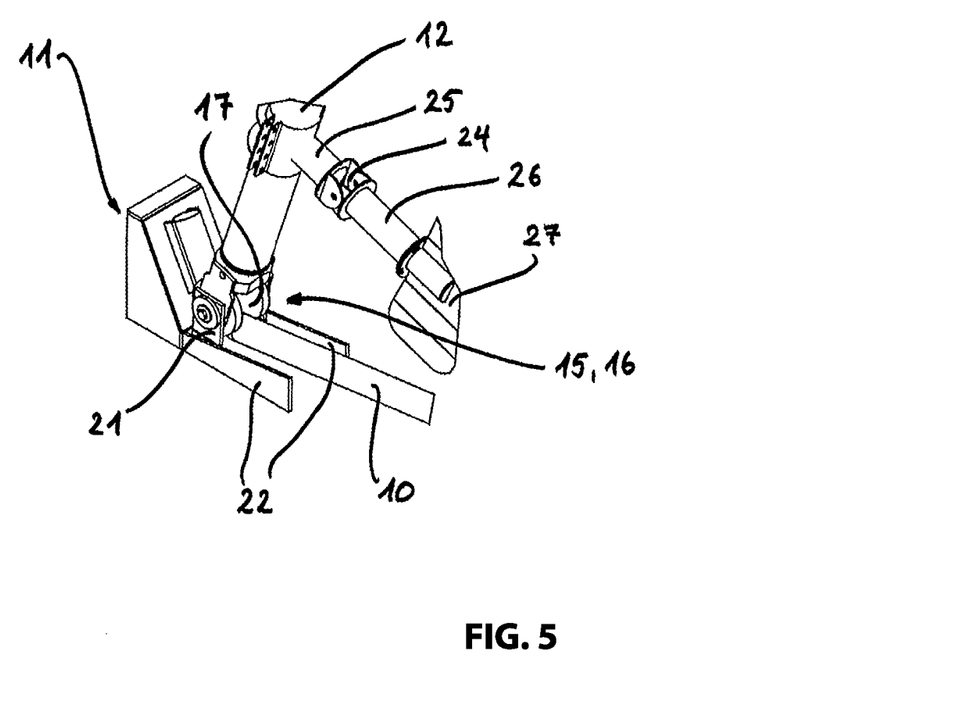
FIG. 5 illustrates a detail of a rolling element bearing of the mixing device according to the invention and a receiving device of the container according to the invention.

Furthermore the receiving device 11 is configured so that the running roller 17 runs so to speak up to a "contact surface" which blocks a further movement of the running roller 17 in a direction that is oriented away from the wall 4 of the fermenter 2. This contact surface is technically implemented in the illustrated embodiment in that the support tube 10 is angled and forms a "lowest spot" in this manner into which the running roller 17 rolls and then cannot move anymore without additional outer force application. In particular an unintentional movement "back" this means in a direction of the wall 4 of the fermenter 2 is not possible since the weight of the mixing device 1 presses the mixing device 1 into the formed lowest spot of the receiving device 11. This way the mixing device 1 is fixated with respect to its position thus with respect to its movements that could occur parallel to the base plate 3 of the container 2, and also with respect to a rotation of the support device 15.

Fixating the support device 15 and the receiving device 11 can be done without tools. This has the consequence that the described form locking engagements do not require any additional actions by an assembly technician or any other facilitations. This configuration facilitates that the mixing device 1 can be installed in a particularly simple manner and also uninstalled in a particularly simple manner without a technician having to interfere at the lower end of the mixing device 1. This has the consequence that the mixing device 1 can be installed or uninstalled also during operation of the bio gas plant, this means even when the fermenter 2 is filled with substrate. In particular uninstalling the mixing device 1 according to the invention is possible in a very simple manner since the mixing device 1 only has to be pulled out from the receiving device 11 in a vertical upward direction and can then be removed through the mounting opening 18 from the container 2.

When moving the rolling element support 16 along the support device 9 the upper end of the mixing device 1 remains essentially in its prior position, wherein the drive device 13 viewed from the inner cavity 7 of the container 2 remains above the mounting opening 18. However, since the upper end of the mixing device 1 does not change its position at all or does not change its position by a considerable amount, however the lower end configured as bearing device 15 is moved, this yields a slanted position of the mixing device 1. This slanted position is particularly well recognizable in FIGS. 2-4. The advantages of this slanted arrangement can be explained particularly well using the illustration according to FIG. 2. From FIG. 2 it is apparent that the plate unit 6 of the two piece ceiling device only has a relatively short extension in a direction perpendicular to the wall 4 of the fermenter 2. This is particularly advantageous in as far as a force reaction of the bearing forces acting at the upper end of the mixing device 1 into the wall 4 of the fermenter 2 is the easier, the closer the force introduction of the mixing device 1 into the wall 4 is provided. The force introduction of bearing forces of the mixing device 1 is performed through an attachment of the mixing device 1 at the plate unit 6. A threaded connection of a flange that envelops the shaft 12 with the plate unit 6 is particularly suitable. Mounting the upper end of the mixing device 1 close to the wall is thus facilitated by the slanted arrangement of the mixing device 1 since the individual mixing elements 14 are arranged at a particular distance to the wall 4 in spite of the close arrangement of the upper end of the mixing device 1 at the wall 4. The reason is that the mixing elements 14 are arranged distributed along the shaft 12 wherein due to the slanted arrangement of the shaft 12 a distance of the mixing elements 14 from the wall 4 is the greater, the closer the mixing elements 14 are arranged relative the base plate 3 of the fermenter 2. This increased distance relative to the upper end of the mixing device 1 facilitates on the one hand side to start operating the mixing device 1 at all. In case the mixing device 1 were oriented vertically starting from its upper end, the mixing elements 14 would contact the wall 4 during operation of the mixing device 1. On the other hand side the mixing effect of the mixing elements 14 due to the slanted arrangement or the increased distance of the mixing elements 14 from the wall 4 is not limited to an edge portion of the fermenter 2. Instead the mixing elements 14 function at a certain distance from the wall 4 so that the mixing effect can also be registered in a center portion of the container 2. Put differently, the slanted arrangement of the mixing device 1 facilitates a combination of the advantage of a support of the upper end of the mixing device 1 proximal to the wall with a mixing effect of the mixing elements 14 remote from the wall. An inclination of the mixing device 1 relative to vertical is approximately 20° in the illustrated embodiment. Other values, however, are conceivable. This applies in particular for the case where the upper end of a mixing device is not supported in a plate unit but in a wall of a respective fermenter.

In order to simplify attaching the upper end of the mixing device 1 at the plate unit 6, the plate unit 6 is arranged inclined relative to horizontal in the portion of the mounting opening 18 as evident in particular from the figures. The angle between an opening plane of the mounting opening 18 and horizontal thus corresponds to the inclination angle of the shaft 12 of the mixing device 1 relative to vertical and thus amounts to approximately 20°.

Figure 4:
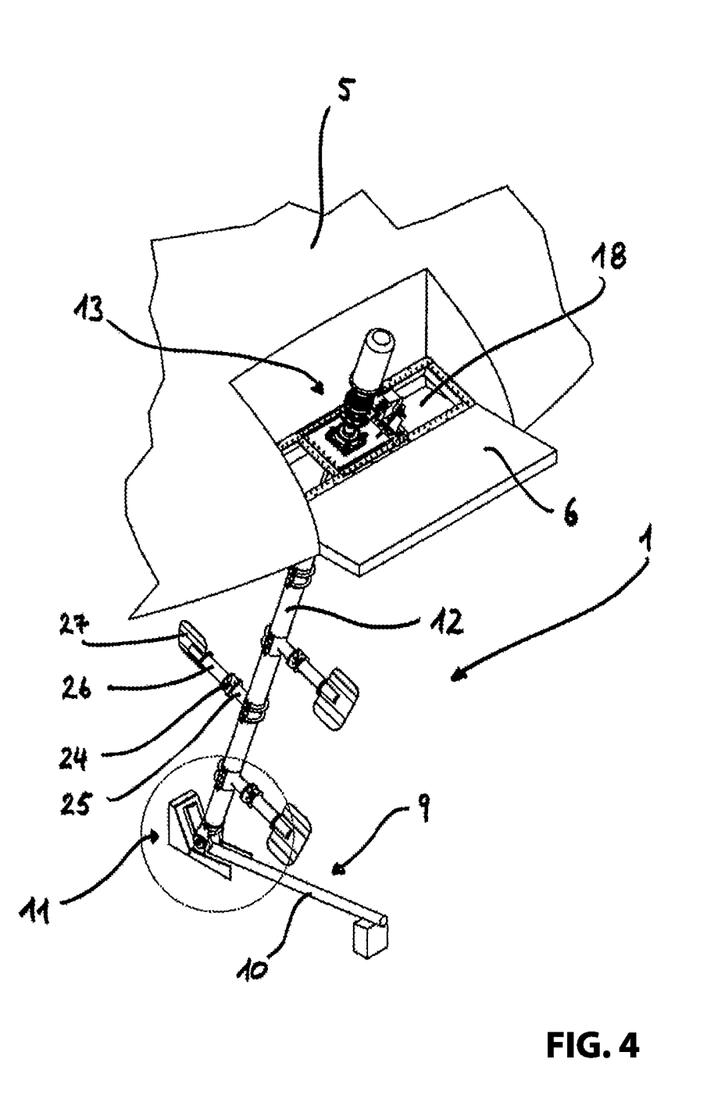
FIG. 4 is an illustration analogous to FIG. 3, however from a different perspective.

Dividing the ceiling device of the fermenter 2 into two elements is particularly apparent from FIG. 4 which illustrates a slanted view of the mixing device 1 from an outside of the fermenter 2, wherein the components of the fermenter 2 itself are not illustrated. Particularly visible is the plate unit 6 including the mounting opening 18 and the membrane unit 5. The membrane unit 5 is connected circumferentially gas tight at the wall 4 of the fermenter 2 and only "interrupted" at this location, this means not connected to the wall 4 where a plate unit or the plate unit 6 is arranged. At the location where the plate unit 6 is arranged the connection between the membrane unit 5 and the wall 4 is interrupted and the membrane unit 5 is connected instead with the plate unit 6 gas tight along a circumferential edge of the plate unit. The plate unit 6 is also gas tight. In this operating condition of the container this applies furthermore to the mounting opening 18 of the plate unit 6 which is essentially closed gas tight. This way the plate unit 6 and the membrane unit 5 jointly form the essentially gas tight ceiling device of the fermenter 2.

The advantage of this subdivision is in particular that a plate unit 6 is used only to a relatively small extent. This is only required because the mixing device 1 has to be supported at its upper end. This, however, cannot be facilitated with the membrane unit 5 since the membrane unit 5 cannot transfer support forces. Besides that the plate unit is rather detrimental since its installation and its design are rather complex. This applies in particular for bio gas plants whose containers are completely closed by a plate shaped ceiling device. Ceiling devices of this type have to be individually planned for each fermenter and need to be produced in a complex manner. By comparison membrane units can be installed in a significantly simpler and faster manner and require significantly less planning, however, they do not facilitate receiving bearing forces wherein fermenters which use membrane units of this type have mixing devices which are inserted from one side of the container through its wall into the interior cavity and which are supported in the wall. This causes the disadvantages already recited supra. In spite of that there is a long felt need to use a membrane unit as a ceiling device. The subdivision of the ceiling unit according to the invention into at least one membrane element and at least one plate element solves the problem of force reaction not being possible and combines the advantages of the respective components.

Another particularity of the mixing device according to the invention is connecting the mixing device elements 14 to the shaft 12. The mixing device elements 14 are thus formed as rectangular paddle elements 27. The paddle elements 27 are connected by support devices 23 with the shaft 12 in a force transferring manner. The support devices 23 respectively include a link device 24. The link device 24 facilitates to adjust an angle of attack of the respective paddle element 27 relative to the shaft 12. This is particularly evident for the upper most mixing device element 14' in FIG. 2. The link device 24 is thus arranged along the support device 23 and is typically oriented so that a portion 25 oriented towards the shaft 12 and a portion 26 of the support device 23 oriented away from the shaft 12 are oriented in parallel. Rotating both elements 25, 26 relative to one another is facilitated the link device 24. This has in particular the effect that a "length" of the support device 23 that is measured perpendicular to the longitudinal axis of the shaft 12 is reduced the more the two components 24, 26 of the support device 23 are rotated relative to one another. In the illustrated embodiment this effect is used to assure that the upper most mixing element 14 during its rotation about the longitudinal axis of the shaft 12 does not accidentally impact the wall 4 of the fermenter 2. Depending how much the shaft 12 is inclined relative to vertical and at which elevation the mixing elements are arranged along the shaft 12 this type of angulation of the support device 23 can be necessary in order to prevent a collision of the respective paddle element with a respective wall. Furthermore a change of the orientation of the paddle element 27 relative to the shaft 12 can be useful in order to assure that the paddle element 27 does not exit from the substrate arranged in the fermenter 2 during a rotation about the longitudinal axis of the shaft 12.

Figure 6:
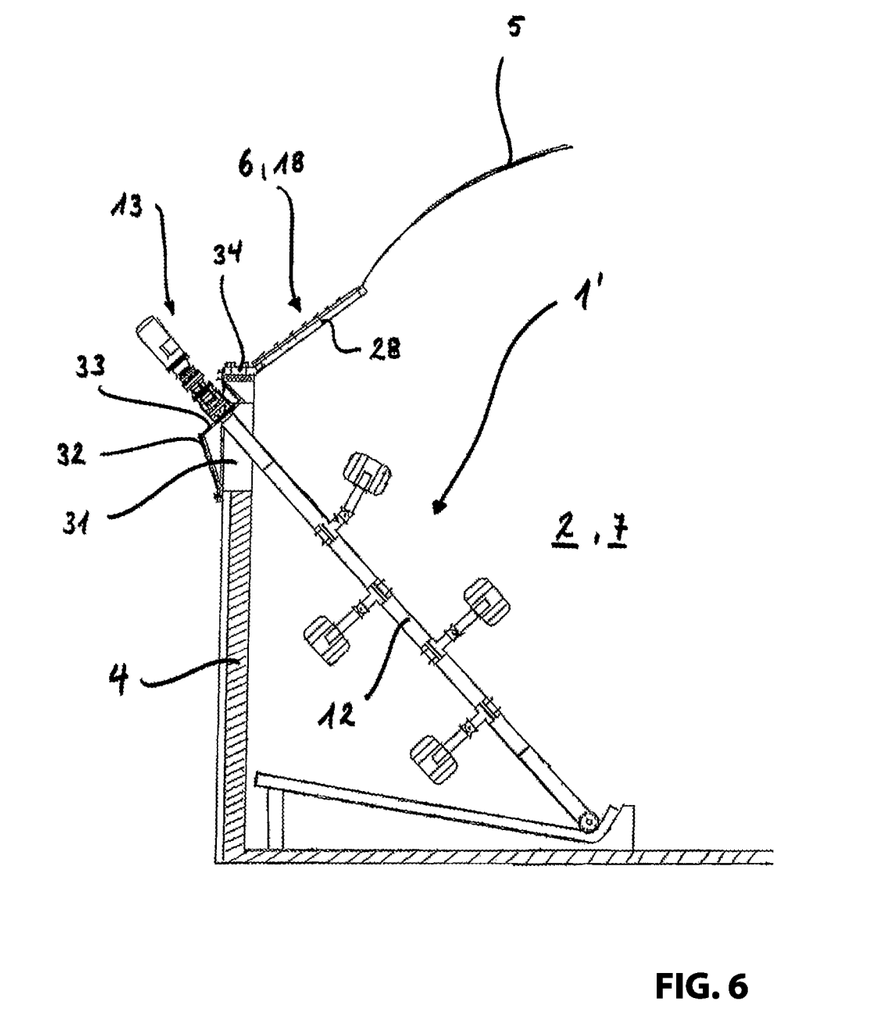
FIG. 6 illustrates a lateral view of another embodiment of the mixing device in operating position.
Figure 7:
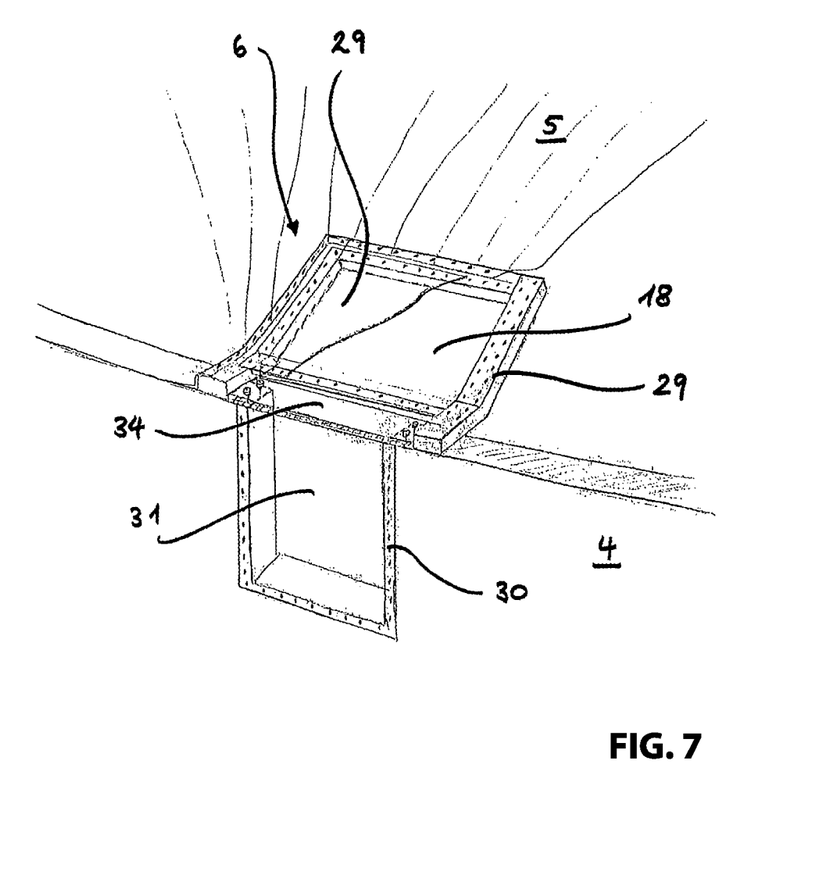
FIG. 7 illustrates a detail of an installation opening of the second embodiment of the mixing device.

In another embodiment that is illustrated in FIG. 6 a mixing device 1' according to the invention is mounted in the fermenter 2 so that the shaft 12 of the mixing device 1' penetrates the wall 4. A detail of a respective installation opening can be derived from FIG. 7. Differently from the mixing device 1 the alternative mixing device 1' is arranged at a higher slant angle relative to vertical. An inclination angle of the shaft 12 is approximately 50° in this case. Furthermore the installation process of the mixing device 1' is identical to the installation process for the mixing device 1. This is also the reason why a ceiling device of the illustrated fermenter 2 is also formed by a type of plate unit 6' in this case and furthermore formed by a membrane unit 5. The plate unit 6' is thus not used for supporting the upper end of the mixing device 1' and to react bearing forces but it is exclusively used for mounting or dismounting purposes. Therefore the ceiling unit 6' is only formed by a mounting opening 18 through which the mixing device 1' can be lowered into the fermenter 2 or lifted out the fermenter 2. The mounting opening 18 is particularly easily visible in FIG. 7. It includes a rigid frame 28 which is essentially closeable gas tight with a cover 29, wherein FIG. 7 illustrates the cover 29 only partially as an example. The membrane unit 5 is connected with the frame 28 in a sealing manner so that no gas can exit the interior 7 of the fermenter 2 at the transition from the plate unit 6' to the membrane unit 5.

After lowering the mixing device 1' through the mounting opening 18 into the fermenter 2 the support device 15 starting from an initially vertical mounting position (the entire mixing device is thus suspended at a lifting device) is moved into its installed position through the rolling element support which includes the running roller 17 and which is arranged at the support device. This method step is identical to installing the mixing device 1 recited supra. Subsequently the upper end of the mixing device 1' is moved laterally out of the mounting opening 18 into a wall frame 30 in which it is eventually attached. The wall frame 30 forms a support opening 31 in which the mixing device 1' is attachable so that support forces can be reacted and received by the wall 4 of the fermenter 2. A transition from the mounting opening 18 into the support opening 31 is open during the mounting of the mixing device 1'. As soon as the upper end of the mixing device 1' is attached in the bearing opening 31 the mixing device 1' is in its operating position. The attachment is performed by fixation plates 32 which are simultaneously connected with the wall frame 30 and also with a bearing plate 33 of the mixing device 1', wherein the bearing plate 33 is arranged directly under the drive device 13 of the mixing device 1'. As soon as the mixing device 1' is in its operating position the mounting opening 18 as well as the bearing opening 31 are essentially closed gas tight. A transition between the mounting opening 18 and the bearing opening 31 is closed with a plank 34 which is bolted onto an opposite side of the wall 4. This is evident from FIG. 7.

This type of attachment of the mixing device 1' in the wall 4 has the advantage that the ceiling device is free of mixing devices during operation of the fermenter 2. The required space for the mounting opening 18 is rather small so that a greater portion of the ceiling device is formed by the membrane unit 5. Thus the fermenter 2 has a height of approximately 10 meters.

REFERENCE NUMERALS AND DESIGNATIONS 1, 1' mixing device
2 fermenter
3 base plate
4 wall
5 membrane unit
6, 6 plate unit
7 interior cavity
8 ambient
9 guide device
10 guide tube
11 receiving device
12 shaft 13 drive device
14, 14' mixing elements
15 support device
16 rolling element support
17 running roller
18 mounting opening
19 width
20 distance
21 blocking plate
22 wall element
23 support device
24 link device
25 component
26 component
27 paddle element
28 frame
29 cover
30 wall frame
31 support opening
32 fixating plate
33 support plate
34 plank

What is claimed is:

1. A method for installing a mixing device in a container, comprising the steps:

supporting a support device of at least one mixing device in a receiving device of the at least one mixing device, which receiving device is connected with a base plate of the container, which support device is arranged at and connected with an end of a shaft of the at least one mixing device, which end is oriented towards the base plate of the container;

initially inserting the support device into a guide device of the at least one mixing device starting from a mounting position of the at least one mixing device in order to insert the support device of the at least one mixing device into the receiving device and guiding the support device through the guide device in a direction towards the receiving device which is arranged at an end of the guide device until the support device reaches the receiving device and is received by the receiving device so that the at least one mixing device enters an installed position;

supporting the at least one mixing device in an upper support section of the at least one mixing device which upper support section is oriented away from the base plate; and increasing an angle between a vertical direction and a longitudinal axis of the shaft when transferring the at least one mixing device from the mounting position into the installed position, wherein the angle in the installed position of the at least one mixing device is between 5° and 60°.

2. The method according to claim 1, wherein the at least one mixing device is vertically lowered into the container from a top side of the container at a distance of 2.0 m at the most that is orthogonally measured from a wall surface of a wall of the container, and wherein an end of the at least one mixing device that is oriented away from the base plate of the container is moved perpendicular to the wall surface of the wall of the container in a direction towards a center portion of the container and fixated after the support device has reached its installed position.

3. The method according to claim 1, wherein the at least one mixing device is lowered into the container through a mounting opening which is arranged in a ceiling device of the container and the at least one mixing device is subsequently fixated in a support opening which is arranged in a wall of the container, so that the at least one mixing device takes its operating position.

* * * * *